United States Patent [19]

Croom, Jr. et al.

[11] Patent Number: 4,857,534

[45] Date of Patent: * Aug. 15, 1989

[54] METHOD OF MAINTAINING RUMINANTS ON HIGH ENERGY LOW FIBER DIET

[75] Inventors: Warren J. Croom, Jr., Cary; Winston M. Hagler, Jr., Raleigh, both of N.C.

[73] Assignee: North Carolina State University, Raleigh, N.C.

[*] Notice: The portion of the term of this patent subsequent to Mar. 24, 2004 has been disclaimed.

[21] Appl. No.: 8,638

[22] Filed: Jan. 12, 1987

Related U.S. Application Data

[63] Continuation-in-part of Ser. No. 596,929, Apr. 5, 1984, Pat. No. 4,652,571.

[51] Int. Cl.[4] .................. A61K 31/44; A61K 31/415; A61K 31/40; A61K 31/27
[52] U.S. Cl. .................................. 514/299; 514/397; 514/413; 514/478
[58] Field of Search ................ 514/413, 299, 397, 478

[56] References Cited

PUBLICATIONS

"Slaframine, a Toxin Causing Salivation, Lacrimation, Urination, and Defecation", p. 1287 in *Veterinary Pharmacology and Therapeutics*, edited by Jones, Booth and McDonald, (Fourth Edition, The Iowa State University Press, 1978).

"Parasympathomimetic, Parasympatholytic, and Autonomic Ganglionic Blocking Agents" (extracts), by Adams, pp. 136-148, 163-164 in *Veterinary Pharmacology and Therapeutics*, edited by Jones, Booth and McDonald (Fourth Edition, The Iowa State University Press, 1978).

"Rizoctonia Leguminicola-Slaframine" by S. D. Aust, pp. 98-109 in *Mycotoxins*, edited by I. F. H. Purchase (Elsevier Publication Company, 1974).

"Effect of Slaframine on Exocrine Gland Function" S. D. Aust, pp. 427-433 in vol. 19 *Biochemical Pharmacology* (Pergamon Press, 1970).

"Drugs Affecting Digestion and Absorption" (extracts), by Phillips and Lewis, pp. 711, 723-725 in *Veterinary Pharmacology and Therapeutics*, edited by Jones, Booth and McDonald (Fourth Edition, The Iowa State University Press, 1978).

"New Drug Stimulates Exocrine Glands; Might Help Cystic Fibrosis Patients" in *News and Comment from The Institute of Biology and Medicine, Michigan State University*, vol. 4, No. 4 (Apr. 1968).

"Chemistry and Physiology of Slaframine", pp. 449-457 in *Mycotoxic Fungi, Mycotoxins, Mycotoxicoses*, edited by WYllie and Morehouse (Marcel Dekker, Inc., N.Y., 1977).

"Lysine Metabolism and Slaframine Biogenesis" by F. P. Guengerich, 30 Fed. Proc. 1067 (1971) (Abstracts 84).

"Salivary Syndrome in Horses: Identification of Slaframine in Red Clover Hay" by Hagler and Behlow, pp. 1067-1073 in vol. 42 of *Applied and Environmental Microbiology* (Dec. 1981).

"A Method for Investigating Salivation in Cattle Using Pilocarpine as a Sialagogue" by Gurnsey, Jones and Reid, pp. 33-41 in *N. Z. Journal of Agricultural Research*, vol. 23 (1980).

"Low-Fat Milk, Displaced Abomasum and Their Relationship to the Feeding of High-Grain, Low-Fiber Diets to Lactating Dairy Cows" by Croom, pp. 59-62, in 1980 *Report, Department of Animal Science, North Carolina State University*.

"Physiological Changes in Ruminants Being Fed High Energy Feeds" by Dougherty, pp. 49-60 in *Buffers in Ruminant Physiology and Metabolism*, edited by Weinberg and Sheffner (Church & Dwight Company, Inc., 1975).

"Bovine Saliva: Production and Function" by E. E. Bartley, pp. 61-77 in *Buffers in Ruminant Physiology and Metabolism*, edited by Weinberg and Sheffner (Church & Dwight Company, Inc., 1976).

"The Use of Buffers in the Rations of Lactating Dairy Cows" by C. L. Davis, pp. 51-64 in *Regulation of Acid-Base Balance*, (Church & Dwight Company, Inc., 1979).

"Manipulation of Rumen Fermentation in Sheep by Increasing the Rate of Flow of Water from the Rumen" by Harrison, Thomson and Osbourn, 85 *J. Agric. Society*, 93-101 (1975).

"Effects of Administration of Glucocorticoids on Pancreas and Growth of Dairy Calves" by Pelletier and Dunnigan, 66 *J. Dairy Science*, 1329, 1336 (1983).

"Inhibition of Enzyme Secretion and Autophagy of Secretory Granules Caused by Action of High Concentration of Secretory Hormones on Rat Pancreatic Slices"; pp. 359-378 in vol. 23, Chapter 23, *Methods in Cell Biology*, by Savion and Selinger, (1981).

(List continued on next page.)

Primary Examiner—Frederick E. Waddell
Attorney, Agent, or Firm—Bell, Seltzer, Park & Gibson

[57] ABSTRACT

This invention relates to the use of parasympathomimetic compounds, their precursors, salts and metabolites, to alter the digestive process in livestock so as to increase the efficiency of food utilization while simultaneously reducing the risk of certain disorders frequently associated with high energy diets. Specifically, the invention comprises administration to ruminants and other livestock of low level dosages of a parasympathomimetic compound to increase salivation during feeding and rumination, thereby increasing rumen digesta turnover rates and efficiency of food utilization while reducing the risk of certain digestive tract disorders such as acidosis and displaced abomasum.

8 Claims, No Drawings

PUBLICATIONS

"The Digestive Enzymes of the Pancreas: A Mixture of Inconstant Proportions", pp. 373-389 in vol. 39 *Ann. Rev. Physiol.*, by Rothman (1977).

"The Role of Nicotinic Receptors in Dog Pancreatic Exocrine Secretion", pp. 623-628 in vol. 78 *Br. J. Pharmac.*, by Devaux, Diaz, Kubota, Magee and Sarles, (1983).

"The Cholinergic Neurotransmitter System", p. 171, in *Chemical Neurobiology-An Introduction to Neurochemistry*, by Bradford.

"Effect of Mineral Salts, Carbachol, and Pilocarpine on Nutrient Digestibility and Ruminal Characteristics in Cattle", pp. 592-600, in *J. Dairy Sci.*, vol. 70, by Wiedmeier, Arambel, Lamb and Marcinkowski (1987).

"Effect of Orally Administered Pilocarpine on Ruminal Characteristics and Nutrient Digestibility in Cattle", pp. 284-289, vol. 70, No. 2, *Journal of Dairy Science*, by Wiedmeier, Arambel, and Walters (1987).

METHOD OF MAINTAINING RUMINANTS ON HIGH ENERGY LOW FIBER DIET

CROSS-REFERENCE TO RELATED APPLICATION

This application is a continuation-in-part of copending application Ser. No. 596,929, filed April 5, 1984, now U.S. Pat. No. 4,652,571, issued Mar. 24, 1987.

FIELD OF THE INVENTION

This invention relates to the use of parasympathomimetic compounds, their precursors, salts and metabolites, to alter the digestive process in livestock so as to increase the efficiency of food utilization while simultaneously reducing the risk of certain disorders frequently associated with high energy diets. Specifically, the invention comprises administration to ruminants and other livestock of low level dosages of a parasympathomimetic compound to increase salivation during feeding and rumination, thereby increasing rumen digesta turnover rates and efficiency of food utilization while reducing the risk of certain digestive tract disorders such as acidosis and displaced abomasum.

BACKGROUND OF THE INVENTION

Rapid production systems currently employed with respect to cattle, sheep and other domestic ruminants typically entail intensive use of relatively expensive high energy feedstuffs to maximize growth rates. Examples include any feedstuffs having a high starch content or a high percentage of total digestive nutrients (TDN). Usually, these feedstuffs contain relatively large quantities of grain or other finely ground energy and protein sources. Although these feedstuffs are almost always high in potential energy content, they differ substantially in fiber content from the grasses, roughage and other forages which it is generally believed ruminants evolved to consume.

As a result, stresses are created in the digestive tracts of ruminants which are maintained on relatively high energy, low fiber diets. The nature and collective age of the microbial population which exists in the rumen in a symbiotic relationship with the animal can be detrimentally altered, leading to increased production of volatile fatty acids and a subsequent increase in systemic acid load. In severe cases, these stresses can lead to acute digestive dysfunctions, such as acidosis, displaced abomasum and other pathological conditions. However, even in mild, subclinical cases, these stresses decrease the efficiencies with which ruminants digest and utilize high energy feedstuffs. Ultimately, inefficiencies are created in the overall production system, and they are compounded by both the expense of underutilized, high energy or high protein feedstuffs and the cost where veterinary or other corrective treatment is required.

Insufficient salivation, brought about by the relatively minimal chewing necessary to consume fine particulate, high energy feedstuffs has previously been recognized as a primary cause of many of these disorders. It has been reported that saliva is the source of up to 70% of the total water flux through the rumen as well as the principal source of ruminal buffering agents. Additionally, it is known that high energy diets promote increased production of volatile fatty acids. Thus, animal scientists have recognized that a significant decrease in ruminant salivation can lead to excess acidity, decreased digesta flow to the small intestine, a slower rate at which dietary nutrients are washed out of the rumen into the small intestine and an alteration in the nature and collective age of the microbial population which exists in the rumen in symbiosis with the host animal.

Heretofore, practical efforts to address the problems arising from feeding ruminants a high energy diet have tended toward treatment of symptoms rather than finding cures or true preventatives. In large part, these efforts have focused upon increasing the fiber content of feedstuffs or upon supplementing high energy diets with salts, minerals or buffering agents such as sodium chloride, calcium chloride, limestone, various bicarbonates and bentonites. While these measures have been of some assistance in enhancing rumen digesta turnover and in controlling excess acidity as well as some of the other digestive dysfunctions associated with high grain diets, they have been substantially less than completely successful.

It is known that parasympathomimetic compounds are effective in stimulating the secretion of saliva and pancreatic fluid in ruminants and other animals. However, these compounds have been subject to a lack of reliable information and predictability regarding the amount of salivation they induce and as to whether they can be administered repeatedly to animals over a prolonged period. Additionally, these compounds have been reported to produce other undesirable effects, such as diarrhea, increased urination and decreased heart and respiratory rates. Some of these compounds have been reported to be toxic and have been the subject of significant efforts to purify certain feedstuffs. Thus, prior to this invention, parasympathomimetic compounds had not been adopted for maintaining any animals on any diet.

We have discovered that low level dosages of a parasympathomimetic compound can be administered to cattle and other ruminants over prolonged periods of time so as to increase rumen digesta turnover rates and alter a variety of other rumen parameters in ways which are quite beneficial to livestock maintained on relatively high energy, low fiber diets. Moreover, we have discovered that, when administered to ruminants in accordance with this invention, the parasympathomimetic compound does not produce pathological conditions.

SUMMARY OF THE INVENTION

A primary object of this invention is to provide a method for maintaining ruminants on a relatively high grain, low fiber diet while reducing the risks of acidosis, displaced abomasum and other digestive dysfunctions.

Another object of this invention is to provide a practical method, through the use of low level dosages of parasympathomimetic compounds, for increasing salivation of ruminants and to do so in a controlled manner, without debilitating side effects.

Another object of this invention is to provide a method for increasing digesta flow from the rumen, thus increasing the rate at which nutrients are washed out of the rumen into the lower digestive tract, thereby increasing the efficiency of high energy feedstuff utilization by ruminants.

Still another object of this invention is to regulate the extent and rate of microbial growth in the rumen by controlling pH of rumen digesta and rumen digesta flow.

We have found that, when low level dosages of parasympathomimetic compounds are administered to ruminants at about the time of feeding, they can be maintained indefinitely on high energy, low fiber diets without suffering digestive tract disorders. Depending upon its specific identity and state at the time of administration (i.e., whether in free base, salt or other forms), the parasympathomimetic compound can be administered intramuscularly, intraperitoneally, intravenously, subcutaneously or orally. By stimulating the exocrine glands and by increasing salivation on a significant scale but in a controlled manner, these compounds decrease the risk of rumen dysfunction. Additionally, they increase water flux through the rumen, and rumen digesta turnover rates, thereby decreasing the risk of displaced abomasum. Furthermore, an exciting finding is that the parasympathomimetic compound alters the rumen environment in such a manner as to promote more efficient use of relatively costly high energy feedstuffs.

Parasympathomimetic compounds have effects which are essentially equivalent to the effects of postganglionic parasympathetic nerve impulses. As such, they produce the same qualitative effects as stimulation of the parasympathetic nervous system does naturally. These effects are mediated through muscarinic acetylcholine receptors, and parasympathomimetic compounds therefore may be also described as muscarinic receptor agonists. Compounds which have been reported as having parasympathomimetic (muscarinic) activity in animals are relatively few in number, namely the following:

| | |
|---|---|
| Bethanecol (Urecholine) | Arecoline |
| Methacholine | Aceclidine |
| Carbachol (Carbamylcholine) | Slaframine |
| Oxotremorine | Tremorine |
| Pilocarpine | Acetylthiocholine |
| Muscarine | |

See Goodman et al., *The Pharmacological Basis of Therapeutics*; Jones et al., *Veterinary Pharmacology and Therapeutics*; H. F. Bradford, *Chemical Neurobiology: An Introduction to Neurochemistry* 1986, p. 171. All parasympathomimetic compounds appear suitable for use in the present invention.

DESCRIPTION OF PREFERRED EMBODIMENTS

Of the known parasympathomimetic compounds, pilocarpine, carbacol and slaframine are preferred for use in accord with this invention, and have been shown to produce favorable results when administered to ruminant animals maintained on a high energy diet. Particularly suitable is slaframine (1-acetoxy-6-aminooctahydroindolizine), one of the naturally occurring indolizine alkaloids produced by the asporogenous fungus *Rhizoctonia leguminicola*.

The parasympathomimetic compound is administered in an amount insufficient to produce a refractory condition (such that the animal fails to respond to various stimuli) but sufficient to increase salivation and the digesta flow from the rumen. Generally, a dosage range of about 12-24 micrograms per kilogram, body weight, injected intramuscularly once every 8-12 hours has been found satisfactory, with 15-20 micrograms pr kilogram, body weight, once every 8-12 hours, being the optimum dosage range in cattle. In most ruminants, this dosage may be repeated at regular intervals, or administered as a continuous subcutaneous implant or inunction with recurrent effectiveness and without undesirable effects on feed intake, heart rate, respiratory rate or kidney output.

The effects on various ruminal parameters of red clover containing 7 micrograms per gram slaframine when fed to four sheep consuming a pelleted, high energy diet is shown in Table I. Addition of slaframine altered the rumen environment and increased the acetate/propionate ratio by 27–44%, rumen fluid turnover rate by 35–38% and salivary flow by 24–36%.

TABLE I

Effects of Daily Feeding of Various Amounts of Red Clover Hay Continuing Slaframine on Ruminal Acetate/Propionate, Fluid Turnover Rate, Volume and Salivary Flow in Wethers Fed a Pelleted Grain Diet

| Item | Red Clover Hay Fed (g/day)[a] | | | |
|---|---|---|---|---|
| | Control[b] | 25 | 50 | 100 |
| Acetate/Propionate | 2.14 | 2.18 | 2.72 | 3.08 |
| Rumen fluid turnover rate (% hour) | 5.28 | 6.48 | 7.30 | 7.12 |
| Salivary flow (ml/24 hr) | 2534 | 2258 | 3450 | 3142 |

[a]Red clover hay contained 7 ug of slaframine.
[b]Control = 50 g of ground alfalfa pellets daily.

The effects of slaframine administered intramuscularly on resting salivary flow rate in Angus steers is shown in Table II. Results confirm data obtained from wethers (Table I) and demonstrate the practicality of obtaining controlled increases in salivary flow in steers. In steers, resting salivary flow accounts for a minimum of 50–80% of total flow. The steers were fed a high energy diet at about twice maintenance--roughly equivalent to feed lot levels.

TABLE II

Effect of Intramuscular Injection of Graded Doses of Pure Slaframine on Resting Salivary Flow in Angus Steers

| Dosage (ug/kg BW) | Time in relationship to dosing (hr) ml/min | | | |
|---|---|---|---|---|
| | −2 to −1 | +.5 to 3.5 | +4.5 to 6.5 | +7.5 to 8.5 |
| 0 | 37.8 | 44.8 | 36.1 | 39.2 |
| 6 | 30.7 | 42.7 | 37.0 | 36.2 |
| 12 | 37.1 | 57.1 | 49.7 | 40.2 |
| 24 | 34.7 | 62.8 | 53.6 | 43.2 |
| Significance | NS | .01 | .01 | NS |

Steers fed high energy, low fiber diet 24 × daily at twice maintenance levels.

No undesirable effect on feed intake, heart rate, respiratory rate or kidney output was observed.

Pure slaframine is a colorless oil which is unstable on exposure to air. It is, however, stable as the free base in such as chloroform and methylene chloride. Salts of slaframine, such as the picrate, dipicrate, citrate, hydrochloride, sulfate and tartrate salts are generally more stable; and most of them are suitable for prolonged storage. The dipicrate may be the most stable, but the free base must be regenerated and separated from the picric acid before the drug can be administered to animals. The other salts are ideal for storage and preparations can be administered directly to animals either orally or by injection in buffered saline. The chemical structure of slaframine is as follows:

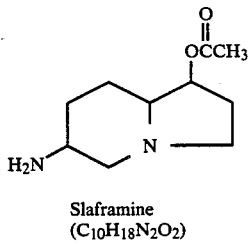

Slaframine
($C_{10}H_{18}N_2O_2$)

Slaframine must be activated in the animal's body, apparently in the liver, to exert its parasympathomimetic effects. This phenomenon is also of great benefit in achieving sustained release of the active metabolite and extending the duration of effectiveness of the administered drug. Because one mole of ammonia is liberated per mole of slaframine during activation, a deamination yielding the compounds A and B, below, is the metabolic mechanism leading to the metabolite of slaframine which has been reported to be the active parasympathomimetic agent, 1-keto-6-aminooctahydroindolizine, ($C_8H_{15}N_2O$), compound B, below:

A.

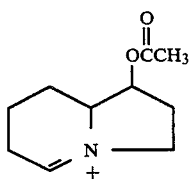

B.

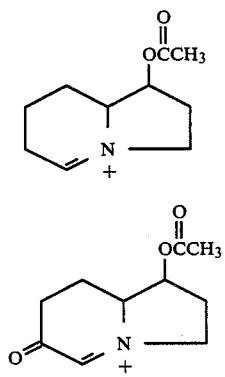

1,6-dihydroxyoctahydroindolizine 1-keto-6-aminooctahydroindolizine See Aust, *Rhizoctonia leguminicola*-Slaframine, pp. 97–109 in *Mycotoxins*, edited by I. F. H. Purchase (Elsevier Scientific Publishing Company, N.Y. 1974).

The biosynthetic pathway through which *R. leguminicola* generates slaframine has been shown to include the cyclization of lysine to pipecolic acid then further biochemical modifications to form the apparently nonparasympathomimetic 1-hydroxy-6-aminooctahydroindolizine which is then acetylated to yield the strongly active slaframine. See Aust, S.D. 1965 Doctoral Thesis, University of Illinois; Guengerich, "Lysine and Slaframine Biogenesis," 30 Fed. Proc. 1067 (1971). Inclusion of serine, lysine, pipecolic acid into the growth medium for *R. leguminicola* has been shown to stimulate the production of slaframine, which, however, is not secreted into the growth medium but retained in the mycelium. This greatly facilitates isolation and purification because extraction of large amounts of liquid culture filtrate has been shown to be unnecessary. Yields of 3-5 mg/g mycelial dry weight have been achieved with slaframine accumulation paralleling growth. Swainsonine may be separated from slaframine by a countercurrent extraction using methylene chloride and partitioning against water at a pH of 10.

Two publications in the early 1970's reported successful chemical synthesis of slaframine. Cartwright, Gardner and Rinehart, "Synthesis of Slaframine," 92 Journal of the *American Chemical Society* 7615 (1970); Gensler and Hu, "Synthesis of D, L-Slaframine," 38 *Journal of Organic Chemistry* 3848 (1973). However, routes to chemical synthesis are presently less efficient than slaframine production by fermentation. There is considerable information on biological production of slaframine by fermentation as well as the chemistry of slaframine so that the potential for large-scale production of this alkaloid drug is great. The potential for strain modification to increase efficiency of fermentations through biotechnology is also great, given the low costs and high yields presently obtained using systems developed for other natural fungal products such as penicillin or zeranol (Ralgro).

That which is claimed is:

1. A method of maintaining a ruminant on a relatively high energy, low fiber diet, said method comprising administering to said ruminant a parasympathomimetic compound or its salts, at a dosage insufficient to produce a refractory condition but sufficient to (a) increase salivation, (b) increase water flux through the rumen, and (c) increase the rate of flow of digesta from the rumen, whereby the risks of acidosis and displaced abomasum are decreased.

2. The method of claim 1 wherein said dosage of said parasympathomimetic compound is 12-24 micrograms per kilogram, body weight, administered once every 8-12 hours.

3. The method of claim 1 wherein said administering to said ruminant is by subcutaneous implant or inunction, said implant or inunction having a release rate equivalent to intramuscular injection, once every 8–12 hours, of 12–24 micrograms per kilogram, body weight.

4. A method of maintaining a ruminant on a relatively high energy, low fiber diet, said method comprising administering to said ruminant a muscarinic receptor agonist or its salts, at a dosage insufficient to produce a refractory condition but sufficient to increase salivation and water flux through the rumen whereby the rate of flow of digesta is increased and the risks of acidosis and displaced abomasum are decreased.

5. The method of claim 1 wherein said administering to said ruminant is by oral administration.

6. The method of claim 1 wherein said administering to said ruminant is by intramuscular injection.

7. The method of claim 1 wherein said administering to said ruminant is by intraperitoneal administration.

8. The method of claim 1 wherein said administering to said ruminant is by intravenous injection.

* * * * *